United States Patent [19]

Arnold

[11] Patent Number: 5,612,285
[45] Date of Patent: Mar. 18, 1997

[54] GLYPHOSATE HERBICIDE FORMULATION

[75] Inventor: Kristin A. Arnold, Kirkwood, Mo.

[73] Assignee: Monsanto Company, St. Louis, Mo.

[21] Appl. No.: 463,447

[22] Filed: Jun. 5, 1995

Related U.S. Application Data

[62] Division of Ser. No. 922,715, Jul. 31, 1992.

[51] Int. Cl.$^6$ ............................ A01N 25/12; A01N 57/02
[52] U.S. Cl. .......................... 504/206; 71/DIG. 1
[58] Field of Search ......................... 504/206; 71/DIG. 1

[56] References Cited

U.S. PATENT DOCUMENTS

| | | | |
|---|---|---|---|
| 4,172,714 | 10/1979 | Albert | 71/93 |
| 4,464,194 | 8/1984 | Prisbylla | 71/87 |
| 4,931,080 | 6/1990 | Chan et al. | 71/87 |
| 5,169,429 | 12/1992 | Warner et al. | 71/92 |
| 5,474,971 | 12/1995 | Sandell | 504/116 |

*Primary Examiner*—S. Mark Clardy
*Attorney, Agent, or Firm*—Mark F. Wachter; Monsanto Company; Arnold, White & Durkee

[57] ABSTRACT

This invention relates to a herbicidal novel dry free-flowing, non-dusty, non-sticky water-soluble granular composition most preferably prepared by extrusion which comprises (a) solid N-phosphonomethylglycine and/or one or more liquid salts thereof or mixtures thereof, (b) one or more liquid surfactants and (c) an extrusion aid which is solid at ambient temperature, the extrusion aid which further comprises a polyalkylene glycol in which the alkylene oxide units are ethylene oxide, propylene oxide, butylene oxide or a mixture of such oxides.

34 Claims, No Drawings

GLYPHOSATE HERBICIDE FORMULATION

This application is a divisional of U.S. Ser. No. 07/922,715 filed Jul. 31, 1992, now pending.

FIELD OF THE INVENTION

This invention relates to a novel dry free-flowing, non-dusty, non-sticky water-soluble granular glyphosate based composition prepared by extrusion which comprises (a) a herbicidally effective amount of N-phosphonomethylglycine and/or one or more agriculturally acceptable water soluble salts thereof or mixtures thereof, (b) one or more surfactants in an effective amount and (c) an effective amount of an extrusion aid which comprises a polyalkylene glycol in which the alkylene oxide units are ethylene oxide, propylene oxide, butylene oxide or a mixture of such oxides.

This invention also relates to processes for preparing and to a herbicidal method of using glyphosate compositions of this invention to kill or control unwanted vegetation by applying an aqueous solution of the composition of this invention to the plants to be killed or controlled.

DESCRIPTION OF THE PRIOR ART

Glyphosate (N-phosphonomethylglycine) is well known as an effective herbicide. Glyphosate, an organic acid, is relatively insoluble in water. Therefore, glyphosate is typically formulated and applied as agriculturally acceptable water-soluble salts, for example as the isopropylamine (IPA) salt, sodium salt or ammonium salt.

Various useful formulations of glyphosate are disclosed in U.S. Pat. Nos. 3,799,758 and 4,405,531 both of which are incorporated herein by reference. Roundup® herbicide, an aqueous concentrate formulation comprising the IPA salt of glyphosate, is made and sold by Monsanto Company and is diluted in water by the end user prior to application. Kusatoban® herbicide, a water-soluble granule (WSG) formulation comprising the monoammonium salt of glyphosate, is made and sold by Monsanto Company in Japan and is dissolved in water by the end user prior to application. Roundup® WSD (water soluble dry), Pacer® and Rival® herbicides are examples of WSG formulations comprising the monoammonium salt of glyphosate made and sold by Monsanto Company similar fashion to Kusatoban.

Glyphosate herbicides are normally applied with a surfactant to improve leaf wetting and assist in penetration of the active ingredient into the leaf. Most commonly the surfactant is employed as an inert ingredient in the formulation.

Many classes of surfactant have been disclosed in compositions with glyphosate, but they show large differences in the degree to which they improve or potentiate the activity of glyphosate. Wyrill and Burnside (Weed Science Volume 25, pages 275–287, 1977) concluded from a wide-ranging study of surfactants as adjuvants for the IPA salt of glyphosate that an effective surfactant is a critical component of any glyphosate spray mixture.

The term "surfactant" as used herein refers to a product in the physical form as supplied by the manufacturer. Generally such products are not preparations of a single chemical species but are instead mixtures of similar species. Any reference herein to physical or chemical properties of any surfactant is intended to apply to the product as so supplied by the manufacturer.

Polyalkylene glycols, especially polyethylene glycols (PEGs) are used commercially in many applications. They are formulated for the cosmetic and pharmaceutical industries in creams, lotions, cakes, sticks and powders. They are used as mold release agents in tableting. They are used as dispersing agents in dyeing. They are used as anti-static agents and, in the agricultural industry, they are used as antifreeze agents and humectants.

EPO patent application 0 206 537 ("'537," published Sep. 20, 1989) discloses solid, phytoactive compositions of glyphosate, methods of use and methods of preparation of such compositions. In Example X thereof, powder #3 is disclosed to have been prepared from 42.5 g of 58% aqueous glyphosate-trimesium, 1 g of silica and 15 grams of polyethylene glycol with an average molecular weight of 7500. This is not a fully water soluble composition as disclosed herein, as it contains a water insoluble ingredient (silica). No water soluble composition containing high molecular weight PEG is disclosed in '537. It is assumed that the applicants of '537 were unable to formulate an acceptable solid composition of a glyphosate herbicide and high molecular weight PEG without the use of silica as an adsorbent for the PEG.

While '537 discloses that mixtures of various nonionic surfactants or mixtures of nonionic surfactants with cationic, anionic or amphoteric surfactants can also be used therein, so long as these surfactants are solid at ambient temperatures, it does not disclose or render obvious applicant's herbicidally efficacious composition comprising a high molecular weight PEG and one or more surfactants which are liquid at ambient temperatures with a glyphosate based active ingredient as may be employed herein. Indeed, '537 discloses therein that a glyphosate composition containing high molecular weight PEG showed low herbicidal activity relative to a liquid glyphosate formulation based on a lower amount of a surfactant described as "Ethoquad 12".

U.S. Pat. No. 4,183,740 ('740) issued to Choong-Gook Jang on Jan. 15, 1980 discloses solid herbicidal compositions comprising a molecular dispersion of a liquid nonionic surfactant in herbicidal pyrazolium salts and a process for preparing the same. On page 2, lines 33–35 of the '740 patent, PEG having an average molecular weight of 6000, a melting range of 60°–63° C. and a viscosity at 210° F. of 700–900 centistokes is disclosed as being useful as a "bulking/absorbing agent" for pyrazolium compositions.

Dry glyphosate formulations have advantages over a liquid product in that (1) any spill from a dry product is easier to clean up than spill from a liquid product, (2) there is potential for less chemical exposure to the end user from using a dry formulation, (3) it is easier to develop residue-free packages and unit-dose packages with a dry product, (4) there is greater potential to develop package mixes with other active ingredients in the case of a dry product and (5) many environmentally or toxicologically attractive surfactants are physically incompatible with glyphosate salts in a liquid formulation.

To realize these advantages for dry glyphosate formulations, the dry product is most conveniently provided in granular form typically coming from an extruder as extrudate.

Numerous methods of preparing granules have been described and are well known to those skilled in the art, but one that is particularly advantageous in producing a high-quality, uniform product with good process controllability is an extrusion process.

The composition of the material being extruded strongly influences the ease with which the product will extrude and the properties of the resulting granules. The presence of a substantial amount of certain surfactants, especially those which are liquid at ambient temperature, may make extrusion difficult or impossible or lead to a soft, sticky granular product which does not flow freely and tends to clump or cake on storage. This has hitherto placed severe limitations on the choice of surfactants for dry glyphosate products.

To one skilled in the art, surfactants which are solid at ambient temperature, as used for example in the compositions disclosed in '537 and similarly in U.S. Pat. No. 4,140,513 issued to Erhard J. Prill on Feb. 20, 1979 will generally be suitable for making free-flowing granules. In '537, page 4, lines 25–28, it is stated that it is particularly important that the surfactant is solid at ambient temperatures and that in practical terms it must be solid at the highest temperatures to which the formulation may be exposed before it is mixed with diluent by the end user. Such temperatures are generally up to about 50° C. It is therefore unexpected from '537 that a surfactant (or surfactant mixture) which is liquid at temperatures below 50° C. when employed in a glyphosate based composition with a suitable extrusion aid could be extruded to a free-flowing, substantially non-caking granular product which applicant has invented.

Dry glyphosate formulations containing surfactants which are liquid at ambient temperature are disclosed in PCT US/89/5793, but it is noted in that publication that surfactants employed therewith which do not gel when added to water do not in general yield good quality granules.

Many of the surfactants or surfactant mixtures which are effective potentiators of glyphosate herbicidal activity and have desirable toxicological or environmental properties are supplied as liquids at ambient temperature and do not gel when added to water. Nothing in the prior art is believed available to guide one of skill in the art in arriving at applicant's composition and method of preparation of free-flowing, non-caking granular formulations containing such surfactants in amounts adequate to provide a high level of glyphosate herbicidal performance as applicant has done.

SUMMARY OF THE INVENTION

This invention relates to a novel dry free-flowing, not, dusty, non-sticky water-soluble granular glyphosate based composition prepared by extrusion which comprises (a) a herbicidally effective amount of N-phosphonomethylglycine and/or one or more salts thereof or mixtures thereof, (b) one or more surfactants in an effective amount and (c) an extrusion aid which in an effective amount further comprises a polyalkylene glycol in which the alkylene oxide units are ethylene oxide, propylene oxide, butylene oxide or a mixture of such oxides.

The dry compositions of this invention may contain a small amount of water from about 0 to about 1.5 per cent by weight.

This invention also relates to processes for preparing and to a herbicidal method of using glyphosate compositions of this invention to kill or control unwanted vegetation by preparing an aqueous solution containing a composition of this invention and then applying an aqueous solution of a composition of this invention to the plants to be killed or controlled.

As used herein, the term "glyphosate herbicide" includes glyphosate which can be present in its acid form, as well as to glyphosate in the form of any water-soluble agriculturally acceptable salt or derivative thereof, which provides glyphosate acid or glyphosate anions in a solution of a herbicidal composition according to this invention.

Preferably the glyphosate employed herein is a relatively non-hygroscopic water-soluble glyphosate salt such as an alkali metal, for example sodium, salt, or ammonium salt of glyphosate or a mixture(s) thereof, although any salts of glyphosate which are able to be formulated in a water-soluble dry form, or mixtures of any such salts or a mixture of glyphosate acid and any such salts, may be employed if desired. Most preferred are mono alkali metal salts of N-phosphonomethylglycine and the mono ammonium salt of N-phosphonomethylglycine or mixtures thereof and the like.

Surfactants of virtually any class may be used. One of the advantages of this invention is that surfactants can be employed without regard to their physical properties. However, the greatest benefit of this invention is realized when the surfactants chosen are supplied as liquids at ambient temperature and are strong potentiators of glyphosate activity. Examples of surfactants which may be useful include alkanolamides, betaine derivatives, ethoxylated propoxylated block copolymers, glycerol esters, glycol esters, imidazolines and imidazoline derivatives, lanolin derivatives, lecithin derivatives, tertiary or quaternary polyoxyalkylene alkylamines, polyoxyalkylene and non-polyoxyalkylene alkylamine oxides, polyoxyalkylene alkylethers, polyoxyalkylene alkylarylethers, polyoxyalkylene alkylesters, alkoxylated and non-alkoxylated sorbitan esters, alkyl glycosides, alkyl polyglycosides, sucrose esters, sucrose glycerides, alkyl sulfates or phosphates, olefin sulfonates, alkylaryl sulfonates, polyoxyalkylene alkylether sulfates or phosphates, sulfosuccinate derivatives, sulfosuccinamates, taurates, sulfates and sulfonates of oils, fatty acids, alcohols, alkoxylated alcohols, fatty esters and aromatic derivatives, mixtures thereof and the like. Those skilled in the art will recognize that other surfactants not included above may be equally useful.

The extrusion aid employed herein comprises an effective amount of a polyalkylene glycol which is solid at ambient temperature and in which the alkylene oxide units are ethylene oxide, propylene oxide, butylene oxide or a mixture of such oxides and the like. Preferably the extrusion aid is a polyethylene glycol (PEG) having an average molecular weight above about 1000 and more preferably a PEG having an average molecular weight from about 3000 to about 15000, for example about 6500 to about 9500 and most preferably from about 7000 to about 9000.

The resulting product of this invention is shelf-stable, substantially non-dusty, free-flowing and substantially non-caking. The product can be easily used by the user and dissolves readily in water prior to its use to kill/control unwanted vegetation.

Prior art problems overcome by compositions of this invention include (1) restriction on choice of surfactant imposed by physical properties of the surfactant; (2) poor efficiency of extrusion, leading to higher cost of manufacture and hence higher cost to the end user; (3) poor handling properties of granules, especially stickiness and a tendency to cake. While prior art shows that high molecular weight PEG (PEG 7500), when used as the sole inert ingredient with glyphosate salt (and water), is an ineffective potentiator of glyphosate herbicidal activity, compositions of this invention containing PEG surprisingly retain high biological efficacy.

DETAILED DESCRIPTION OF THE INVENTION

This invention relates to a novel dry free-flowing, non-dusty, non-sticky water-soluble granular glyphosate based composition most preferably prepared by extrusion which comprises (a) a herbicidally effective amount of N-phosphonomethylglycine and/or one or more salts thereof or mixtures thereof, (b) one or more surfactants in an effective amount and (c) an extrusion aid in an effective amount which is solid at ambient temperature, the extrusion aid which further comprises a polyalkylene glycol in which the alkylene oxide units are ethylene oxide, propylene oxide, butylene oxide or a mixture of such oxides.

This invention also relates to processes for preparing and to a herbicidal method of using glyphosate compositions of this invention to kill or control unwanted vegetation by applying an aqueous solution of the composition of this invention to the plants to be killed or controlled.

Preferably the glyphosate employed herein is in the form of an alkali metal, for example sodium, salt or the ammonium salt or a mixture thereof, although any salts of glyphosate which are able to be formulated in a water-soluble dry form, or mixtures of any such salts or a mixture of glyphosate acid and any such salts, may be employed if desired. Most preferably the glyphosate is present as the mono alkali metal or mono ammonium salt.

The most preferable glyphosate salt useful herein is the monoammonium salt as contained for example in Roundup® WSD herbicide from Monsanto Company.

Typically the compositions of this invention contain from about 40 to about 90 per cent by weight of glyphosate salt, more preferably from about 60 to about 85 per cent by weight of glyphosate salt, although greater or lesser amounts may be employed if desired.

Surfactants of virtually any class may be used; however, the greatest benefit of this invention is realized when the surfactants chosen are supplied as liquids at ambient temperature. Examples of surfactants useful in formulations of this invention are alkanolamides, betaine derivatives, ethoxylated propoxylated block copolymers, glycerol esters, glycol esters, imidazolines and imidazoline derivatives, lanolin derivatives, lecithin derivatives, tertiary or quaternary polyoxyalkylene alkylamines, polyoxyalkylene and non-polyoxyalkylene alkylamine oxides, polyoxyalkylene alkylethers, polyoxyalkylene alkylarylethers, polyoxyalkylene alkylesters, alkoxylated and non-alkoxylated sorbitan esters, alkyl glycosides, alkyl polyglycosides, sucrose glycerides, sucrose esters, alkyl sulfates or phosphates, olefin sulfonates, alkylaryl sulfonates, polyoxyalkylene alkylether sulfates or phosphates, sulfosuccinate derivatives, sulfosuccinamates, taurates, sulfates and sulfonates of oils, fatty acids, alcohols, alkoxylated alcohols, fatty esters and aromatic derivatives, mixtures thereof and the like.

Preferred surfactants useful in this invention include Ethomeen T/25, Ethoquad C/25 and Ethoquad 18/25 from Akzo Chemicals Inc.; T-Det DD 10 and T-Det DD 14 from Harcros Chemicals Inc.; Rhodafac RE 610 from Rhône Poulenc Corporation; Emcol CC-9 from Witco Corporation; Trydet 2676 and Trycol 5943 from Henkel Corporation; Tergitol 15-S-12 from Union Carbide Corporation; and Tween 20 and Tween 80 from ICI Americas Inc.

The compositions of this invention contain an effective amount of surfactant generally from about 3 to about 30 per cent by weight of surfactant, more preferably from about 5 to about 20 per cent by weight of surfactant, although greater or lesser amounts may be employed if desired.

Typically the compositions of this invention contain an effective amount of extrusion aid generally up to about 30 per cent by weight of the extrusion aid and more preferably from about 1 to about 20 per cent by weight of the extrusion aid, although greater or lesser amounts may be employed if desired. More than one extrusion aid may be employed as well as mixtures thereof if desired.

As to composition of a preferred extrusion aid, typically it is a polyethylene glycol having an average molecular weight greater than about 1000. A polyethylene glycol having an average molecular weight in the range from about 3000 to about 15000, for example from about 6500 to about 9500, and most preferably from about 7000 to about 9000 is most suitably employed.

Examples of preferable extrusion aids useful in this invention are PEG 8000 from Fisher Scientific and Carbowax® Polyethylene Glycol 8000 from Union Carbide Corporation.

Various other inert adjuvants may be employed in effective amount(s) if desired as constituents of formulations of the present invention, including but not limited to agriculturally acceptable inorganic salts, for example ammonium sulfate, ammonium nitrate, monopotassium phosphate, tetrapotassium pyrophosphate, sodium bisulfate, sodium sulfite, ammonium bicarbonate and the like; dispersants; binders; anti-foam agents; dyes and humectants.

Optionally the formulation may also contain water soluble active ingredients in a herbicidally effective amount, other than glyphosate, for example one or more salts of phenoxy herbicides such as MCPA and 2,4-D, dicamba, acifluorfen and the like.

A preferred process for preparing a composition of this invention comprises (1) making a homogeneous mixture of a surfactant(s) and extrusion aid together with a small quantity of water; (2) mixing this homogeneous mixture with a dry particulate form of glyphosate to form a blend; (3) extruding the blend and optionally (4) drying the resulting granules.

An alternative desirable process for making compositions of this invention comprises (1) making a homogeneous mixture of a surfactant(s) together with a small quantity of water; (2) dry mixing glyphosate and extrusion aid, both of which are in dry particulate form; (3) blending the homogeneous mixture product of with the dry mix product of (2); (4) extruding the blend and optionally (5) drying the resulting granules.

Compositions of this invention may be prepared by mixing the various ingredients in the ratios exemplary of those described herein. The processes of this invention may be preferably carried out at room temperatures, except only as noted herein wherein slight heating is advantageous.

The process of this invention may be preferably carried out at atmospheric pressure except where extrusion is practiced.

This invention also relates to a herbicidal method of using compositions of this invention in an effective amount to kill or control unwanted vegetation by applying the composition in aqueous solution to the plants to be killed or controlled. The composition of this invention is preferably dissolved in such a volume of water as to provide a resulting effective concentration of glyphosate acid equivalent in the range from about 0.025 to about 25 and preferably from about 0.5 to about 5 per cent by weight, although those of skill in the art will recognize that greater or lesser degrees of dilution may be employed depending upon the plant species to be killed or controlled, their stage of growth, the weather, the application equipment used and other conditions at the point of application and other factors as well.

Various application methods may be employed including broadcast spraying, directed spraying or wiping the foliage with the dissolved granules of this invention. Depending upon the degree of control desired, the age and species of the plants and the weather conditions, typically the amount of glyphosate is a herbicidally effective amount, (expressed as acid equivalent) applied in the range from about 0.1 to about 10 and preferably from about 0.25 to about 2.5 kg/ha although greater or lesser amounts may be applied.

GENERAL PROCESS DESCRIPTION

All the glyphosate water soluble granule (WSG) formulations containing an extrusion aid prepared according to this invention were made by one of the two general procedures recited below involving unit operations of mixing, extrusion and optionally drying.

In a preferred procedure, the selected desired amount of glyphosate salt preferably Fitz milled in powder form is weighed into any suitable mixing device, for example a food processor, Hobart mixer, ribbon blender, kneader or the like. In a separate container one or more surfactants, normally in liquid form, an extrusion aid (in the form of powder or flakes) and a small amount of water are heated to assist and just bring about dissolution of the extrusion aid. Heating is not sufficient to bring the temperature up to the melting point of the extrusion aid. The mixture is stirred well until it appears homogeneous and is then added to the Fitz milled glyphosate salt and mixed. Mixing time in this step is dependent on the mixing device used and on the quantity of formulation being prepared as illustrated by Examples provided herein.

The resulting blend of glyphosate salt, surfactant(s) and extrusion aid is extruded in any suitable extruder, for example a basket extruder, single screw radial extruder, twin screw radial extruder, single screw front-end extruder or the like. After extrusion the resulting granules optionally may be dried in any suitable drying device such as a fluid bed dryer or the like to a desired lower water content.

In another procedure, dry mixing is done using Fitz milled powdered glyphosate salt and powdered extrusion aid in a mixing device such as any of the types illustratively listed above or the like. In a separate container one or more surfactants, normally in liquid form, and a small amount of water are mixed and added to the dry glyphosate salt/ extrusion aid mixture. The resulting blend is thoroughly mixed, extruded and optionally dried as in the first procedure above. If any of the surfactants gel when added to water, either the surfactant/water mixture is heated to a temperature just to dissolve the gel or the surfactant(s) and water are added separately to the dry glyphosate salt/extrusion aid mixture.

Without being limited, the following Examples are provided of these processes. In all Examples the source of dry monoammonium glyphosate was Roundup® WSD, milled in a Fitz mill to provide a fine powder (40 mesh screen). All granules prepared in the following Examples 1–10 illustrative of this invention were free-flowing, non-dusty and non-sticky and were acceptable high quality herbicidally efficacious products.

All percentages appearing herein are by weight unless otherwise specified.

EXAMPLE 1

75% monoammonium glyphosate

8% Ethomeen T/25 (Akzo Chemicals Inc.) as surfactant

17% Carbowax® Polyethylene Glycol 8000 (Union Carbide Corporation) as extrusion aid Dry monoammonium glyphosate (75 g) Fitz milled in powder form was weighed into a food processor bowl. Ethomeen T/25 (8 g), Carbowax PEG 8000 (17 g) and water (5 ml) were placed in a 150 ml beaker, heated in a microwave oven for 20 seconds and hand stirred with a spatula until the mixture appeared homogeneous. The resulting blend was added to the dry ammonium glyphosate and mixed thoroughly with a food processor for about 2 minutes. The resulting mixture was extruded in a Luwa KAR-75 bench-top basket extruder and the resulting granules were fluid bed dried in an aeromatic dryer at about 60° C., followed by screening with 10 and 40 mesh screens to remove over- and under-sized particles.

EXAMPLE 2

75% monoammonium glyphosate

10% Ethomeen T/25 (Akzo Chemicals Inc.) as surfactant

15% Carbowax PEG 8000 (Union Carbide Corporation) as extrusion aid

Dry monoammonium glyphosate (75 g) and Carbowax PEG 8000 (15 g), both in powder form, were weighed into a food processor bowl and thoroughly mixed dry, without heating. Ethomeen T/25 (15 g) and water (5 ml) were placed in a 150 ml beaker, heated in a microwave oven for about 10 seconds and hand stirred with a spatula until the surfactant gel which formed on addition of the Ethomeen T/25 to water was thoroughly dispersed. The surfactant/water mixture was then added to the ammonium glyphosate/PEG 8000 mixture and mixed thoroughly with a food processor. The resulting mixture was extruded in a bench-top basket extruder as in Example 1 and the granules were fluid bed dried as in Example 1, followed by screening with 10 and 40 mesh screens to remove over- and under-sized particles.

EXAMPLE 3

75% monoammonium glyphosate

15% Ethoquad 18/25 (Akzo Chemicals Inc.) as surfactant

10% Carbowax PEG 8000 (Union Carbide Corporation) as extrusion aid

Dry monoammonium glyphosate (225 g) in powder form was weighed into a food processor bowl. Ethoquad 18/25 (45 g), Carbowax PEG 8000 (30 g) and water (15 ml) were placed in a 250 ml beaker, heated in a microwave oven for 40 seconds and hand stirred with a spatula until the resulting blend (mixture) appeared homogeneous. This blend was added to the ammonium glyphosate and mixed thoroughly with a food processor. The mixture was extruded in a bench-top basket extruder as in Example 1 and the resulting granules were fluid bed dried as in Example 1, followed by screening with 10 and 40 mesh screens to remove over- and under-sized particles.

EXAMPLE 4

75% monoammonium glyphosate

11% Ethoquad C/25 (Akzo Chemicals Inc.) as surfactant

11% Tween 20 (ICI Americas Inc.) as surfactant

3% Carbowax PEG 8000 (Union Carbide Corporation) as extrusion aid

Dry monoammonium glyphosate (8.5 kg) in powder form was weighed into buckets and added to a 1 cu. ft. Robinson ribbon blender. Ethoquad C/25 (1.2 kg), Tween 20 (1.2 kg), Carbowax PEG 8000 (340 g) and water (570 ml) were mixed in two 2000 ml beakers, heated in a microwave oven for several minutes and hand stirred with a spatula until the mixture appeared homogeneous. The resulting blend was added slowly to the monoammonium glyphosate while the ribbon blender was running. This addition took approximately 5 to 10 minutes. The mixture was blended further for 10 to 15 minutes in the ribbon blender. The mixture was then discharged and extruded in a pilot scale Niro-Aromatic basket extruder. The granules were dried in a fluid bed dryer (Fitz Aire FH-5 at about 60° C.) and screened with 10 and 40 mesh screens to remove over- and under-sized particles.

EXAMPLE 5

75% monoammonium glyphosate

10% Ethoquad C/25 (Akzo Chemicals Inc.) as surfactant

10% T-Det DD 14 (Harcros Chemicals Inc.) as surfactant

5% Carbowax PEG 8000 (Union Carbide Corporation) as extrusion aid

Dry ammonium glyphosate (8.5 kg) in powder form was weighed into buckets and added to a ribbon blender as in example 4. Ethoquad C/25 (1.13 kg), T-Det DD 14 (1.13kg), Carbowax PEG 8000 (567 g) and water (570 ml) were mixed in two 2000 ml beakers, heated in a microwave oven for several minutes and hand stirred with a spatula until the mixture appeared homogeneous. The resulting blend was added slowly to the ammonium glyphosate while the ribbon blender was running. This addition took approximately 5–10 minutes. The mixture was blended for a further 10–15 minutes in the ribbon blender. The mixture was then discharged and extruded in a pilot scale basket extruder as in Example 4. The granules were dried in a fluid bed dryer as in Example 4 and screened with 10 and 40 mesh screens to remove over- and under-sized particles.

EXAMPLE 6

75% ammonium glyphosate

15% Ethomeen T/25 (Akzo Chemicals Inc.) as surfactant

5% Rhodafac RE 610 (Rhône Poulenc Corporation) as surfactant

5% Carbowax PEG 8000 (Union Carbide Corporation) as extrusion aid

Dry ammonium glyphosate (225 g) in powder form was weighed into a food processor bowl. Ethomeen T/25 (45 g), Rhodafac RE 610 (15 g), Carbowax PEG 8000 (15 g) and water (15 ml) were placed in a 250 ml beaker, heated in a microwave oven for 40 seconds and stirred with a spatula until the mixture appeared homogeneous. The resulting blend was added to the ammonium glyphosate and mixed thoroughly with a food processor. The mixture was extruded in a bench-top basket extruder as in Example 1 and the resulting granules were fluid bed dried as in Example 1, followed by screening with 10 and 40 mesh screens to remove over- and under-sized particles.

EXAMPLE 7

75% ammonium glyphosate

8% Emcol CC-9 (Witco Corporation) as surfactant

12% T-Det DD 14 (Harcros Chemicals Inc.) as surfactant

5% Carbowax PEG 8000 (Union Carbide) as extrusion aid

Dry ammonium glyphosate (225 g) in powder form was weighed into a food processor bowl. Emcol CC-9 (27 g), T-Det DD 14 (36 g), Carbowax PEG 8000 (15 g) and water (15 ml) were placed in a 250 ml beaker, heated in a microwave oven for 40 seconds and stirred with a spatula until the mixture appeared homogeneous. The resulting blend was added to the ammonium glyphosate and mixed thoroughly with a food processor. The mixture was extruded in a bench-top basket extruder as in Example 1 and the resulting granules were fluid bed dried as in Example 1, followed by screening with 10 and 40 mesh screens to remove over- and under-sized particles.

EXAMPLE 8

75% ammonium glyphosate

9% Ethoquad 18/25 (Akzo Chemicals Inc.) as surfactant

8% Trydet 2676 (Henkel-Corporation) as surfactant

8% Carbowax PEG 8000 (Union Carbide Corporation) as extrusion aid

Dry ammonium glyphosate (8.5 kg) in powder form was weighed into buckets and added to a ribbon blender as in example 4. Ethoquad 18/25 (1.02 kg), Trydet 2676 (907 g), Carbowax PEG 8000 (907 g) and water (570 ml) were mixed in two 2000 ml beakers, heated in a microwave oven for several minutes and stirred with a spatula until the mixture appeared homogeneous. The resulting blend was added slowly to the ammonium glyphosate while the ribbon blender was running. This addition took approximately 5–10 minutes. The mixture was blended for a further 10–15 minutes in the ribbon blender. The mixture was then discharged and extruded in a pilot scale basket extruder as in Example 4. The granules were dried in a fluid bed dryer as in Example 4 and screened with 10 and 40mesh screens to remove over- and under-sized particles.

EXAMPLE 9

75% ammonium glyphosate

9% Ethoquad 18/25 (Akzo Chemicals Inc.) as surfactant

8% Trycol 5943 (Henkel Corporation) as surfactant

8% Carbowax PEG 8000 (Union Carbide Corporation) as extrusion aid

Dry ammonium glyphosate (8.5 kg) in powder form was weighed into buckets and added to a ribbon blender as in Example 4. Ethoquad 18/25 (1.02 kg), Trycol 5943 (907 g), Carbowax PEG 8000 (907 g) and water (570 ml) were mixed in two 2000 ml beakers, heated in a microwave oven for several minutes and stirred with a spatula until the mixture appeared homogeneous. The resulting blend was added slowly to the ammonium glyphosate while the ribbon blender was running. This addition took approximately 5–10 minutes. The mixture was blended for a further 10–15 minutes in the ribbon blender. The mixture was then discharged and extruded in a pilot scale basket extruder as in Example 4. The granules were dried in a fluid bed dryer as in Example 4 and screened with 10 and 40 mesh screens to remove over- and under-sized particles.

EXAMPLE 10

75% ammonium glyphosate

10% Ethoquad C/25 (Akzo Chemicals Inc.) as surfactant

10% Tergitol 15-S-12 (Union Carbide Corporation) as surfactant

5% Carbowax PEG 8000 (Union Carbide Corporation) as extrusion aid

Dry ammonium glyphosate (225 g) in powder form was weighed into a food processor bowl. Ethoquad C/25 (30 g), Tergitol 15-S-12 (30 g), Carbowax PEG 8000 (15 g) and water (15 ml) were placed in a 250 ml beaker, heated in a microwave oven for 40 seconds and stirred with a spatula until the mixture appeared homogeneous. The resulting blend was added to the ammonium glyphosate and mixed thoroughly with a food processor. The mixture was extruded in a bench-top basket extruder and the resulting granules were fluid bed dried as in Example 1, followed by screening with 10 and 40 mesh screens to remove over- and under-sized particles.

EXAMPLE 11

75% monoammonium glyphosate

10% Ethoquad 18/25 (Akzo Chemicals Inc.) as surfactant

10% T-Det DD 10 (Harcros Chemicals Inc.) as surfactant

5% Carbowax PEG 8000 (Union Carbide Corporation) as extrusion aid

Dry monoammonium glyphosate (8.5 kg) in powder form was weighed into buckets and added to a 1 cu. ft. Robinson ribbon blender. Ethoquad 18/25 (1.13 kg), T-Det DD 10 (1.13 kg), Carbowax PEG 8000 (567 g) and water (570 ml) were mixed in two 2000 ml beakers, heated in a microwave oven for several minutes and hand stirred with a spatula until the mixture appeared homogeneous. The resulting blend was added slowly to the monoammonium glyphosate while the ribbon blender was running. This addition took approximately 5 to 10 minutes. The mixture was blended further for 10 to 15 minutes in the ribbon blender. The mixture was then discharged and extruded in a pilot scale Niro-Aromatic basket extruder. The granules were-dried in a fluid bed dryer (Fitz Aire FH-5 at about 60° C.) and screened with 10 and 40 mesh screens to remove over- and under-sized particles.

EXAMPLE 12

Tests have been conducted using formulations of this invention to determine herbicidal efficacy. These tests taken collectively have generally demonstrated that, contrary to expectations from EP 0 206 537 noted above, inclusion of PEG 8000 as an extrusion aid in applicant's invention does not negatively impact herbicidal efficacy, even when less surfactant is employed.

All compositions below were prepared according to the process described for Example 1 previously.

Composition A

75% ammonium glyphosate

15% Ethomeen T/25 (polyethoxylated [15 moles] tallow amine) (Akzo Chemicals Inc.) as surfactant 10% Carbowax Polyethylene glycol 8000 (Union Carbide Corporation) as extrusion aid Composition B 75% ammonium glyphosate 18% Ethomeen T/25 (Akzo Chemicals Inc.) as surfactant 7% Carbowax PEG 8000 (Union Carbide Corporation) as extrusion aid Composition D 75% ammonium glyphosate 18% T-Det DD 10 (polyethoxylated [10 moles] dodecyl phenol) (Harcros Chemicals Inc.) as surfactant 7% Carbowax PEG 8000 (Union Carbide Corporation) as extrusion aid Composition F 75% ammonium glyphosate 18% T-Det DD 14 (polyethoxylated [14 moles] dodecyl phenol) (Harcros Chemicals Inc.) as surfactant 7% Carbowax PEG 8000 (Union Carbide Corporation) as extrusion aid Composition H 75% ammonium glyphosate 18% Tween 20 sorbitan monolaurate (polysorbate 20) (ICI Americas Inc.) as surfactant 7% Carbowax PEG 8000-(Union Carbide Corporation) as extrusion aid Composition J 75% ammonium glyphosate 18% Tween 80 sorbitan monooleate (polysorbate 80) (ICI Americas Inc.) as surfactant 7% Carbowax PEG 8000 (Union Carbide Corporation) as extrusion aid Compositions of prior art included in the test for comparative purposes were:

Composition C (for comparison with Compositions A and B of this invention)

75% ammonium glyphosate

25% Ethomeen T/25 (Akzo Chemicals Inc.) as surfactant

Composition E (for comparison with Composition D of this invention)

75% ammonium glyphosate

25% T-Det DD 10 (Harcros Chemicals Inc.) as surfactant

Composition G (for comparison with Composition F of this invention)

75% ammonium glyphosate

25% T-Det DD 14 (Harcros Chemicals Inc.) as surfactant

Composition I (for comparison with Composition H of this invention)

75% ammonium glyphosate

25% Tween 20 (ICI Americas Inc.) as surfactant

Composition K (for comparison with Composition J of this invention)

75% ammonium glyphosate

25% Tween 80 (ICI Americas Inc.) as surfactant

As an additional comparative treatment, Roundup® herbicide, a commercial aqueous concentrate formulation from Monsanto Company containing the isopropylamine salt of glyphosate and a surfactant based on tallowamine ethoxylate, was applied at the same glyphosate acid equivalent rates as the above granular compositions illustrative of this invention.

Seeds of downy brome (*Bromus tectorum*) and Indian mustard (*Brassica juncea*) were planted in 10 cm square pots containing soil and fertilizer and placed in a growth chamber. Temperature was maintained at about 18° C. during the day and about 12° C. at night, with a daylength of about 12 hours. After the plants had been growing for 22 days, they were selected for uniformity and assigned to treatments involving the compositions listed above. All compositions were applied in aqueous solution, using an overhead track sprayer calibrated to deliver the equivalent of 94 l/ha of spray solution at a spray pressure of 207 kPa. Two rates were applied for each composition, each rate treatment being replicated three times. The rates selected were 0.28 kg and 0.56 kg glyphosate acid equivalent/ha. No adjuvant was added to the spray solution. After spraying, the plants were returned to the growth chamber under the same conditions as those described above. Herbicidal efficacy was measured 27 days after treatment (DAT) by visual estimation of percent injury by comparison with unsprayed control plants (% inhibition).

Results of the test are shown in Table 1. They show compositions of the present invention to be essentially equal in herbicidal efficacy to compositions of prior art lacking PEG 8000 as an extrusion aid, even where the absence of PEG 8000 is compensated by an equal amount of additional surfactant.

TABLE 1

| | average % inhibition 27 DAT | | | |
|---|---|---|---|---|
| | Downy brome | | Indian mustard | |
| Composition | 0.28 kg/ha | 0.56 kg/ha | 0.28 kg/ha | 0.56 kg/ha |
| A | 72 | 96 | 60 | 77 |
| B | 88 | 97 | 47 | 73 |
| C (Comparative) | 68 | 98 | 60 | 73 |
| D | 83 | 99 | 10 | 50 |
| E (Comparative) | 74 | 97 | 37 | 43 |
| F | 84 | 99 | 17 | 63 |
| G (Comparative) | 89 | 99 | 20 | 50 |
| H | 76 | 98 | 33 | 71 |
| I (Comparative) | 89 | 99 | 28 | 73 |
| J | 68 | 98 | 40 | 50 |
| K (Comparative) COMPARATIVE | 83 | 99 | 30 | 41 |
| Roundup ® | 67 | 97 | 60 | 62 |

Although the invention is described with respect to specific modifications, the details thereof are not to be construed as limitations except to any extent indicated in the following claims.

What is claimed is:

1. A method for making a water-soluble granular herbicidal composition comprising
   (1) forming a homogenous mixture of at least one surfactant and an extrusion aid at a temperature substantially below the melting point of the extrusion aid, wherein the surfactant is liquid at ambient temperature and the extrusion aid comprises at least one polyalkylene glycol in which the alkylene oxide unit is ethylene oxide, propylene oxide or butylene oxide and the polyalkylene glycol has an average molecular weight of from about 1,000 to about 15,000;
   (2) blending the mixture with a dry particulate form of N-phosphonomethylglycine or a salt thereof; and
   (3) extruding the blend to form herbicidal granules.

2. The method of claim 1 wherein the surfactant is an alkanolamide, a betaine derivative, an ethoxylated propoxylated block copolymer, a glycerol ester, a glycol ester, an imidazoline, an imidazoline derivative, a lanolin derivative, a lecithin derivative, a tertiary or quaternary polyoxyalkylene alkylamine, a polyoxyalkylene, a non-polyoxyalkylene alkylamine oxide, a polyoxyalkylene alkylether, a polyoxyalkylene alkylarylether, a polyoxyalkylene alkylester, an alkoxylated sorbitan ester, a non-alkoxylated sorbitan ester, an alkyl glycoside, a sucrose ester, an alkyl polyglycoside, a sucrose glyceride, an alkyl sulfate, an alkyl phosphate, an olefin sulfonate, an alkylaryl sulfonate, a polyoxyalkylene alkylether sulfate, a polyoxyalkylene alkylether phosphate, a sulfosuccinate derivative, a sulfosuccinamate, a taurate, a sulfate, a sulfonate of an oil, a fatty acid, an alcohol, an alkoxylated alcohol, a fatty acid ester, an aromatic derivative of a fatty acid ester or a mixture thereof that is liquid at ambient temperature.

3. The method of claim 2 wherein the surfactant is a tertiary or quaternary polyoxyalkylene alkylamine that is liquid at ambient temperature.

4. The method of claim 1 wherein the polyalkylene glycol is a polyethylene glycol.

5. The method of claim 1 wherein the N-phosphonomethylglycine salt is an isopropylamine, an alkali metal or an ammonium salt of N-phosphonomethylglycine.

6. The method of claim 4 wherein the polyethylene glycol has an average molecular weight from about 3,000 to about 15,000.

7. The method of claim 4 wherein the polyethylene glycol has an average molecular weight of from about 6,500 to about 9,500.

8. The method of claim 4 wherein the polyethylene glycol has an average molecular weight of from about 7,000 to about 9,000.

9. The method of claim 1 wherein the composition contains from about 40 to about 90 percent by weight of an N-phosphonomethylglycine salt.

10. The method of claim 1 wherein the composition contains from about 60 to about 85 percent by weight of an N-phosphonomethylglycine salt.

11. The method of claim 1 wherein the composition contains from about 3 to about 30 percent by weight of surfactant.

12. The method of claim 1 wherein the composition contains from about 5 to about 20 percent by weight of surfactant.

13. The method of claim 1 wherein the composition contains about 20 percent by weight of surfactant.

14. The method of claim 1 wherein the composition contains up to about 30 percent by weight of the extrusion aid.

15. The method of claim 1 wherein the composition contains from about 1 to about 20 percent by weight of the extrusion aid.

16. The method of claim 1 wherein the composition contains from about 3 percent to about 5 percent of the extrusion aid.

17. The method of claim 1 further comprising a step of drying the granules.

18. A method for making a water-soluble granular herbicidal composition comprising
   (1) forming a dry mixture of N-phosphonomethylglycine or a salt thereof and an extrusion aid, wherein both the N-phosphonomethylglycine or salt thereof and the extrusion aid are in a dry particulate form and further wherein the extrusion aid comprises at least one polyalkylene glycol in which the alkylene oxide unit is ethylene oxide, propylene oxide, or butylene oxide and the polyalklyene glycol has an average molecular weight of from about 1,000 to about 15,000;
   (2) blending the mixture with at least one surfactant at a temperature substantially below the melting point of the extrusion aid, wherein the surfactant is liquid at ambient temperature; and
   (3) extruding the blend to form herbicidal granules.

19. The method of claim 18 wherein the surfactant is an alkanolamide, a betaine derivative, an ethoxylated propoxylated block copolymer, a glycerol ester, a glycol ester, an imidazoline, an imidazoline derivative, a lanolin derivative, a lecithin derivative, a tertiary or quaternary polyoxyalkylene alkylamine, a polyoxyalkylene, a non-polyoxyalkylene alkylamine oxide, a polyoxyalkylene alkylether, a polyoxyalkylene alkylarylether, a polyoxyalkylene alkylester, an alkoxylated sorbitan ester, a non-alkoxylated sorbitan ester, an alkyl glycoside, a sucrose ester, an alkyl polyglycoside, a sucrose glyceride, an alkyl sulfate, an alkyl phosphate, an olefin sulfonate, an alkylaryl sulfonate, a polyoxyalkylene alkylether sulfate, a polyoxyalkylene alkylether phosphate, a sulfosuccinate derivative, a sulfosuccinamate, a taurate, a sulfate, a sulfonate of an oil, a fatty acid, an alcohol, an alkoxylated alcohol, a fatty acid ester, an aromatic derivative of a fatty acid ester or a mixture thereof that is liquid at ambient temperature.

20. The method of claim 19 wherein the surfactant is a tertiary or quaternary polyoxyalkylene aklylamine that is liquid at ambient temperature.

21. The method of claim 18 wherein the polyalkylene glycol is a polyethylene glycol.

22. The method of claim 18 wherein the N-phosphonomethylglycine salt is an isopropylamine, an alkali metal or an ammonium salt of N-phosphonomethylglycine.

23. The method of claim 21 wherein the polyethylene glycol has an average molecular weight from about 3,000 to about 15,000.

24. The method of claim 18 wherein the polyethylene glycol has an average molecular weight of from about 6,500 to about 9,500.

25. The method of claim 18 wherein the polyethylene glycol has an average molecular weight of from about 7,000 to about 9,000.

26. The method of claim 18 wherein the composition contains from about 40 to about 90 percent by weight of an N-phosphonomethylglycine salt.

27. The method of claim 18 wherein the composition contains from about 60 to about 85 percent by weight of an N-phosphonomethylglycine salt.

28. The method of claim 18 wherein the composition contains from about 3 to about 30 percent by weight of surfactant.

29. The method of claim 18 wherein the composition contains from about 5 to about 20 percent by weight of surfactant.

30. The method of claim 18 wherein the composition contains about 20 percent by weight of surfactant.

31. The method of claim 18 wherein the composition contains up to about 30 percent by weight of the extrusion aid.

32. The method of claim 18 wherein the composition contains from about 1 to about 20 percent by weight of the extrusion aid.

33. The method of claim 18 wherein the composition contains from about 3 percent to about 5 percent of the extrusion aid.

34. The method of claim 18 further comprising a step of drying the granules.

* * * * *

UNITED STATES PATENT AND TRADEMARK OFFICE
CERTIFICATE OF CORRECTION

PATENT NO: 5,612,285

DATED: March 18, 1997

INVENTOR(S): Kristin A. Arnold

It is certified that error appears in the above-identified patent and that said Letters Patent is hereby corrected as shown below:

add immediately below the section entitled "References Cited, U. S. PATENT DOCUMENTS" on the cover page, the following:

| --3,799,758 | 3/74 | Franz | 71/86 |
| 4,140,513 | 2/79 | Prill | 71/86--. | add immediately following, "4,172,714 10/1979 Albert ........ 71/93 in the section entitled "References Cited, U.S. PATENT DOCUMENTS" on the cover page, the following:

| --4,183,740 | 1/80 | Jang et al. | 71/92 |
| 4,405,531 | 9/83 | Franz | 260/501.12--. | add immediately following, "5,474,971 12/1995 Sandell ........ 504/116 in the section entitled References Cited" on the cover page, the following:

--FOREIGN PATENT DOCUMENTS 501,798    9/02/92         European Pat. Off.

UNITED STATES PATENT AND TRADEMARK OFFICE
CERTIFICATE OF CORRECTION

PATENT NO. : 5,612,285

DATED : March 18, 1997

INVENTOR(S) : Kristin A. Arnold

It is certified that error appears in the above-indentified patent and that said Letters Patent is hereby corrected as shown below:

OTHER PUBLICATIONS

--J.B. Wyrill, III and O.C. Burnside, "Glyphosate Toxicity to Common Milkweed and Hemp Dogbane and influenced by Surfactants", WEED SCIENCE, Vol. 25, Issue 3, pgs. 275-287, May 1977.
PCT/US/89/05793 (Equivalent to EP-A-0206537 published December 30 1986).--

Signed and Sealed this

Twelfth Day of August, 1997

*Attest:*

BRUCE LEHMAN

*Attesting Officer*     *Commissioner of Patents and Trademarks*